US005266315A

United States Patent [19]

Taguchi et al.

[11] Patent Number: 5,266,315

[45] Date of Patent: Nov. 30, 1993

[54] **COMPOSITE FOR *CLOSTRIDIUM DIFFICILE* DIARRHEA AND PSEUDOMEMBRANOUS COLITIS**

[75] Inventors: Nobuhiro Taguchi; Itsuki Fujita, both of Chosei, Japan

[73] Assignee: Kabushiki Kaisha Miyarisan Seibutsu Igaku Kenkyusho, Tokyo, Japan

[21] Appl. No.: 918,883

[22] Filed: Jul. 23, 1992

Related U.S. Application Data

[63] Continuation of Ser. No. 583,561, Sep. 14, 1990, abandoned.

[30] Foreign Application Priority Data

Jul. 5, 1990 [JP] Japan .................................. 2-117267

[51] Int. Cl.$^5$ .............................................. C12N 1/20

[52] U.S. Cl. .................................. 424/93 E; 435/842

[58] Field of Search ........................ 424/93 E; 435/842

[56] References Cited

U.S. PATENT DOCUMENTS 4,892,731 1/1990 Arai et al. ......................... 424/93 E

FOREIGN PATENT DOCUMENTS 2678 7/1964 France .
62-58990 3/1987 Japan .
1190386 5/1970 United Kingdom .

OTHER PUBLICATIONS

*Clostridum butyricum* Prevents Diarrhea caused by an Experimental Antibiotic, Shinyo Taguchi et al., Jpn. Journal of Bacteriology, vol. 43, No. 4, pp. 829-835, 1988.

Studies on the Anti-Diarrheal Activity of *Colostridum butyricum* Miyairi II 588: Effects of *Clostridium butyricum* Miyairi II 588: On the Enterotoxicity of the Enterotoxins Produced by Enterotoxigenic *Escherichia coli*, 1987, p. 55.

*Primary Examiner*—Douglas W. Robinson
*Assistant Examiner*—Jean C. Witz
*Attorney, Agent, or Firm*—Mathews, Woodbridge & Collins

[57] ABSTRACT

A preventive and curative medical composition for *Clostridium difficile* diarrhea and psedomembranous colitis, which composition comprises cells or spores of a butyric acid bacterium and Vancomycin.

4 Claims, No Drawings

COMPOSITE FOR *CLOSTRIDIUM DIFFICILE* DIARRHEA AND PSEUDOMEMBRANOUS COLITIS

This is a continuation of Ser. No. 07/583,561, filed Sep. 14, 1990, now abandoned.

BACKGROUND OF THE INVENTION

1. Field of the Invention

This invention relates to a preventive and curative pharmaceutical composition for *Clostridium difficile* diarrhea and pseudomembranous colitis.

2. Description of the Prior Art

For the cure of *Clostridium difficile* diarrhea and pseudomembranous colitis, the chemotherapy by the use of Vancomycin (VCM), for example, which is strongly active against *Clostridium difficile*, the bacterium causative of the diseases, has been employed to bring about improvement in the remedy of abdominal symptoms such as diarrhea. The *Clostridium difficile* diarrhea, however, forms a spore in the intestinal canal and the spore is resistant to an antibacterial agent and cannot be easily eliminated in spite of an extended application of the chemotherapy by the use of Vancomycin. Since the spore of *Clostridium difficile* which outlives the therapy germinates and propagates again, recurrence of the diseases are diagnosed for the patent. Further, the administration of Vancomycin to a patient for a long period of time has the possibility that the activity of Vancomycin itself against bacteria will further disturb the host's intestinal microflora, induce new infections under the disturbed microflora, and increase the resistance of the pathogenic bacterium to chemicals, for example.

In the short-term administration of Vancomycin, the ratio of survival of spore is high and the consequent frequent recurrences of the disease induce asthenia in the patient. For the cure of the disease under discussion, a desire is expressed to develop a new therapeutic method which comprises a short-term administration of an antibacterial agent such as Vancomycin and a treatment capable of quickly eliminating the surviving spore without obstructing the restoration of intestinal microflora.

An object of this invention, therefore, is to provide a novel preventive and curative pharmaceutical composition for *Clostridium difficile* diarrhea and pseudomembranous colitis.

SUMMARY OF THE INVENTION

The object described above is accomplished by a preventive and curative pharmaceutical composition for *Clostridium difficile* diarrhea and pseudomembranous colitis, which medical composition comprises cells or spores of a butyric acid bacterium and Vancomycin.

This invention, as described above, is directed to a preventive and curative medical composition for *Clostridium difficile* diarrhea and pseudomembranous colitis, which medical composition comprises cells or spores of a butyric acid bacterium and Vancomycin. The administration of this medical composition prevents or cures the diseases and entails an effect of only very low toxicity.

EXPLANATION OF THE PREFERRED EMBODIMENT

The present inventors, with a view to expediting the cure of *Clostridium difficile* diarrhea and pseudomembranous colitis, shortening the period of administration of an antibacterial agent such as Vancomycin, and preventing the recurrence of the diseases, have conducted an experiment comprising inducing diarrhea in Golden hamsters by the administration of Cefatrizine (hereinafter referred to briefly as "CFT"), an antibiotic substance generally known as a morbidity model for the diseases, newly forming a recurrence model after the therapy with Vancomycin on the basis of the symptom of diarrhea, and allowing the affected hamsters to consume orally *Clostridium butyricum* MIYAIRI 588 (hereinafter referred to briefly as "CbM"), one species of butyric acid bacteria by way of remedy. They have found the remedy to produce highly preferable results. This invention has been perfected as the result.

Now, the development which has led to the present invention will be described in detail below. In the recurrence models used, when the administration of Vancomycin was terminated (after 3 days' administration) at a sign of improvement in the fecal condition, the *Clostridium difficile* showed positive culture and was detected in the form of spores. After about 10 days thence, the animals developed diarrhea and died. In the contents of the intestinal tubes of the dead animals, toxicogenic *Clostridium difficile* and the toxin thereof were detected, indicating the recurrence of the disease. When the administration of Vancomycin was continued even after detection of a sign of improvement in the fecal condition (for a total of 10 days), though the *Clostridium difficile* showed negative culture, the animals showed a discernible sign of recurrence of the disease within about 5 days.

In the animals which were given 3 days' administration of Vancomycin, then left to consume for 20 days a feed incorporating therein ground dry cells of CbM in a proportion such that the animals could ingest approximately $10^8$ CFU of the CbM spore per day, and thereafter left to consume a feed containing no CbM, conspicuous decrease of the ratio of recurrence of the diseases and negative culture of Clostridium difficile were attained. The CbM is anaerobic sporal bacterium which propagates and forms spores in an ordinary culture medium under anaerobic conditions. For example, bouillon containing 2% of corn starch is a suitable culture medium for the bacterium. From these results, it is concluded that in the cure of *Clostridium difficile* diarrhea and pseudomembranous colitis, and antibacterial agent such as Vancomycin which is strongly active against *Clostridium difficile* destroys abnormally overpropagated *Clostridium difficile*. Then, the therapy by the administration of ground dry cells of CbM in a daily dose of about $10^9$ CFU/kg is effective.

In the medical composition, the Vancomycin is incorporated in an amount in the range of 1 mg to 10 g, preferably 10 mg to 10 g, based on $10^8$ CFU of the cells or spores of butyric acid bacterium. The medical composition is administered in an amount in the range of $10^6$ to $10^9$ CFU, preferably $10^6$ to $10^8$ CFU, as cells or spores of butyric acid bacterium per kg of human body weight. This composition is orally administered to human beings or animals, when necessary, in a form combined with a pharmaceutically acceptable carrier.

The term "butyric acid bacterium" refers to a microorganism which yields butyric acid as the product of its metabolism. Among other species of butyric acid bacteria, *Clostridium butyricum* proves to be particularly desirable.

The medical composition of this invention exhibits extremely low acute and chronic toxicity.

Now, this invention will be described more specifically below with reference to working examples. *Clostridium butyricum* MIYARIRI 588 used in the experiments has been deposited at Fermentation Research Institute under FERM-BP 2789 and *Clostridium difficile* Ha. 16 similarly used has been deposited at the same institute under FERM-BP 2877.

EXAMPLE 1

Morbidity models of recurring *Clostridium difficile* diarrhea were produced by orally administering a suspension of 4.5-mg potency of CFT in 0.2 ml of purified water with the aid of a catheter five Golden hamsters (60 g, male). After the CFT treatment, the animals were put under observation. When any of the animals showed a sign of fecal abnormality such as diarrhea or loose passage, a solution of 3-mg potency of Vancomycin in 0.2 ml of purified water was orally administered to that animal six times with 12 hours' intervals. All of the treated animals were put under observation. Their rectal feces were sampled along the course of time. The samples were anaerobically cultured for bacterial isolation in a CCFA culture medium (37° C., 72 hrs). The isolated *Clostridium difficile* was placed in a BHI broth and again cultured therein (37° C., 48 hrs). In the resultant culture broth, the bacterium was tested for toxin-producing ability by the use of a latex reagent [the D-1 toxin of *Clostridium dificile* can be detected at 500 ng/ml (sample)]. Further, diarrhea feces of live hamsters and intestinal tube contents of dead hamsters were tested for presence or absence of toxin.

In Table 1, the D-1 toxin of *Clostridium difficile* detected in the intestinal tube contents of dead hamsters, the lethal activity of the toxin on healthy hamsters, and the presence of a toxin-producing isolated strain possessing the behavior of Table 2 (*Clostridium difficile* Ha. 16) in an amount of $1.4 \times 10^8$ CFU/g are shown. As shown in Table 3, the administration of 6 doses of Vancomycin brought about discernible improvement in the fecal state but was not so effective as to show negative culture of *Clostridium difficile*. Six to 11 days after termination of the administration of Vancomycin, all of the animals died of recurrent diarrhea. The limit of detection of *Clostridium difficile* from feces was 400 CFU/g (feces).

EXAMPLE 2

Long-term administrations of Vancomycin and administrations of CbM were tried for the purpose of preventing the recurrent *Clostridium difficile* diarrhea and effecting quick elimination of *Clostridium difficile* from the interior of the intestinal tube. In the experiment, five animals were treated in the same manner as in Example 1 (A group), five animals were subjected to administration of 14 doses of VCM subsequently to the treatment of Example 1 (B group). and five animals were treated in the same manner as in Example 1, then allowed to consume for 17 days a feed incorporating therein ground dry cells of CbM in such a proportion as to allow ingestion of 1 to $5 \times 10^8$ CFU of CbM spores per day, and thereafter allowed to consume an ordinary feed containing no CbM (C group) were set. After the treatment, all of the animals were put under observation. From their intestinal feces, *Clostridium difficile* was isolated. The bacterium thus isolated was tested for detection of D-1 toxin. The culture (37° C., 72 hrs.) for isolation of CbM was anaerobically carried out in a 5% horse blood BL Agar containing 350 mg of Cycloserine, 1 mg of Kanamycin, 75 μg of Clindamycin, and 12 mg of Trimethoprim each per liter of the culture medium.

As shown in Table 4, B group, i.e. the group of long-term administration of Vancomycin, when compared with A group 48 hours after termination of administration, showed improvement in the fecal state and a discernible decrease of the ratio of *Clostridium difficile* detection (one of five animals). In all of the animals under test, the disease recurred after 5 to 8 days following the termination of the long-term administration of Vancomycin. This is because in the intestinal tube endowed with a subaxenic condition by the long-term administration of Vancomycin, a small number of spores normally prevented from propagation by the intestinal microflora were allowed to germinate and propagate easily. Thus, B group failed to attain complete cure of the disease inclusive of the prevention of recurrence of the disease. In contrast, in C group, i.e. the group of CbM administration, as shown in Table 5, though the recurrence of the disease was observed in 2 of the total of 5 animals, negative culture of *Clostridium difficile* was finally attained in the remainder of the animals, representing a survival ratio of 60%. The therapy comprising a short-term administration of Vancomycin and a continuous administration of CbM was effective in curbing germination and propagation of *Clostridium difficile* surviving in the intestine without impairing the intestinal microflora and attaining complete cure of the disease inclusive of prevention of the recurrence of the disease.

TABLE 1

Intestinal contents of dead hamsters and toxity of isolated strain (Clostridium difficile Ha. 16) in healty hamsters

| Sample[1] | D-1 toxin | Number of dead animals/ number of treated animals |
|---|---|---|
| N-Fil | − | 0/2 |
| L-Fil | + | 2/2 |
| BHI-Fil | − | 0/2 |
| BHI, Ha. 16-Fil | + | 2/2 |

[1] A suspension prepared by stirring the intestinal content of a hamster in pruified water of an amount three times as large as that of the intestional content and a sterilized filtrate of the culture broth of an isolated strain were intra-abdominally administered each in an amount of 1.0 ml to healthy hamsters (70 g, male). N-Fil (sterilized filtrate of intestinal content of healthy hamster), L-Fil (sterilized filtrate of intestinal content of dead hamster), BHI-Fil (sterilized filtrate of BHI broth), and BHI, Ha; 16-Fil (sterilized filtrate of culture broth obtained by anaerobically culturing isolated strain in BHI broth for 48 hours).

TABLE 2

Biochemical characteristics of Ha. 16 isolated from intestinal content of diarrhea hamster

| | | | |
|---|---|---|---|
| Gram's stain | + | Indole | − |
| Formation of endospores | + | Esclin | + |
| Aerobic growth | − | Lecithinase | − |
| Motility | + | Lipase | − |
| Hemolytic capacity | − | Sugar-utilizing ability | |
| Milk | − | Fructose | + |
| Gelatin | + | Glucose | + |
| Nitrate | − | Mannitol | + |
| Product from PYG | | Mannose | + |
| Acetic acid | + | Xylose | − |
| Butyric acid | + | Lactose | − |
| Iso-butyric acid | + | Maltose | − |
| Valeric acid | + | Starch | − |

TABLE 2-continued

| Biochemical characteristics of Ha. 16 isolated from intestinal content of diarrhea hamster | | | |
|---|---|---|---|
| Iso-valeric acid | + | Sucrose | − |
| Iso-caproic acid | + | | |
| Lactic acid | + | | |

What is claimed is:

1. A medical composition for the treatment of *Clostridium difficile* diarrhea and pseudomembranous colitis, which composition comprises a therapeutically effective amount of the combination of cells or spores of *Clostridium butyricum* and Vancomycin.

TABLE 3

| | | Preparation of recurrence model (N = 5) | | | |
|---|---|---|---|---|---|
| Treated group | Items of test | Before treatment | 24 hrs. after termination of CFT administration | 48 hrs. after termination of administration of 6 doses of VCM | 12 days after termination of administration of VCM |
| A | Cases of discernible sign of diarrhea | 0/5 | 2/5 | 0/5 | 5/5 |
| | Cases of detection of D-1 toxin in feces | 0/5 | 2/5 | 0/5 | 5/5 |
| | Cases of detection of *C. difficile* (Log No. CFU/g feces)[1)] | 0/5 (max. 2.6) | 5/5 (6.6 ± 1.1) | 4/5 (3.9 ± 0.7) | 5/5 (8.0 ± 0.5) |
| | Cases of fatality (average number of days of survival)[2)] | 0/5 | 0/5 | 0/5 | 5/5 (8.0) |

[1)]Detection of *Clostridium difficile* in feces was possible above the level of 400 CFU/g in feces.
[2)]Number of days of survival represents the number of days from the time of termination of administration of 6 doses of VCM to the time of death.

TABLE 4

| | | Results of cure in cases of long-term administration of VCM (N = 5) | | |
|---|---|---|---|---|
| | | | Feces tested | |
| Treated group | Items of test | Before treatment | 48 hrs. after termination of administration of 20 doses of VCM | 9 days after termination of administration of VCM |
| B | Cases of discernible sign of diarrhea | 0/5 | 0/5 | 5/5 |
| | Cases of detection of D-1 toxin in feces | 0/5 | 0/5 | 5/5 |
| | Cases of detection of *C. difficile* (Log No. CFU/g feces)[1)] | 0/5 (max. 2.6) | 1/5 (3.1) | 5/5 (8.0 ± 0.4) |
| | Cases of fatality (average number of days of survival)[2)] | 0/5 | 0/5 | 5/5 (6.8) |

[1)]Detection of *Clostridium difficile* in feces was possible above the level of 400 CFU/g in feces.
[2)]Number of days of survival represents the number days from the time of termination of administration of 20 doses of VCM to the time of death.

TABLE 5

| | | Results of cure by continuous administration of CbM (N = 5) | | | |
|---|---|---|---|---|---|
| | | | Feces tested | | |
| Treated group | Items of test | Before treatment | 48 hrs. after termination of administration of 6 doses of VCM | 7 days after start of administration of CbM | 10 days after termination of CbM[4)] |
| C | Cases of discernible sign of diarrhea | 0/5 | 0/5 | 2/5 | 0/3 |
| | Cases of detection of D-1 toxin feces | 0/5 | 0/5 | 2/5 | 0/3 |
| | Cases of detection of *C. difficile* (Log No. CFU/g feces)[1)] | 0/5 (max 2.6) | 3/5 (3.5 ± 0.9) | 2/5 (8.2) | 0/3 (max. 2.6) |
| | Cases of detection of CbM (Log No. CFU/g of feces)[3)] | 0/5 (max. 2.6) | 5/5 (5.3 ± 0.6) | 5/5 (5.9 ± 0.1) | 0/3 (max 2.6) |
| | Cases of fatality (average number of days of survival)[2)] | 0/5 | 0/5 | 2/5 (8.0) | 0/3 |

[1)]Detection of *Clostridium difficile* in feces was possible above the level of 400 CFU/g in feces.
[2)]Number of days of survival represents the number of days from the time of termination of administration of 6 doses of VCM to the time of death.
[3)]Detection of CbM in feces was possible above the level of 400 CFU/g of feces.
[4)]The data recorded as to 3 animals surviving after the elapse of 7 days from start of administration of CbM.

2. A method for the treatment of *Clostridium difficile* diarrhea and pseudomembranous colitis which comprises administering to an affected human being or animal a composition comprising a therapeutically effective amount of the combination of cells or spores of *Clostridium butyricum* and Vancomycin.

3. The method according to claim 2 wherein the amount of Vancomycin is from about 1 mg to about 10 g per $10^8$ CFU of said cells or spores of *Clostridium butyricum*.

4. The method according to claim 2 wherein the amount of cells or spores of a *Clostridium butyricum* to be used is from about $10^6$ to about $10^9$ CFU per kg of a human body weight.

* * * * *